United States Patent [19]
Palmieri et al.

[11] Patent Number: 5,632,399
[45] Date of Patent: May 27, 1997

[54] SELF-SEALING REAGENT CONTAINER AND REAGENT CONTAINER SYSTEM

[75] Inventors: Thomas Palmieri, Paramus; Arthur L. Babson, Chester, both of N.J.

[73] Assignee: DPC Cirrus Inc., Randolph, N.J.

[21] Appl. No.: 670,994

[22] Filed: Jun. 28, 1996

[51] Int. Cl.$^6$ .................................................. B65D 51/18
[52] U.S. Cl. .......................... 220/253; 220/255; 220/348
[58] Field of Search ................................ 220/253, 255, 220/339, 348

[56] References Cited

U.S. PATENT DOCUMENTS

| | | | |
|---|---|---|---|
| 1,162,791 | 12/1915 | Lubas | 220/253 |
| 3,169,679 | 2/1965 | Hunter | 220/255 |
| 3,392,060 | 7/1968 | Favre | 220/255 |
| 4,673,813 | 6/1987 | Sanchez | 220/253 |
| 4,718,570 | 1/1988 | Diener | 220/253 |
| 5,282,543 | 2/1994 | Picozza et al. | 220/255 |
| 5,316,726 | 5/1994 | Babson et al. | 422/65 |

OTHER PUBLICATIONS

Trade Brochure, entitled "PK310 Fully Automated Enzyme Analyser", a publication of Olympus Biomedical Products Div., Wendenstrasse 14–16, 2 Hamburg 1, Germany, 15 pages, undated.

Primary Examiner—Joseph M. Moy
Attorney, Agent, or Firm—Whitham, Curtis, Whitham & McGinn

[57] ABSTRACT

Self-sealing reagent container, and a system of same on a carousel, related to a vessel having a plurality of separate compartments, each compartment having an opening in an upper surface of the vessel, with a hinged lid member attached to said vessel having spring-like biasing to automatically reseal openings of the vessel after reagent extraction. The lid has a first arm that is normally biased such that its caps cover the compartment openings, but external force can be applied to said first arm to permit the first arm to be translated so as to displace the caps from covering the compartment openings whereby reagent in the compartments can be accessed and withdrawn. Once the reagent extraction is completed and the compartment opening cleared of the extraction device, the normal biasing acting on the first arm of the lid causes it to move back to reseal the caps over the compartment openings. The lid member is used with a ramp guide means to ensure alignment of openings and caps and provide vertical clearance of the first arm relative to the cover of the reagent vessel when displaced by external force.

18 Claims, 5 Drawing Sheets

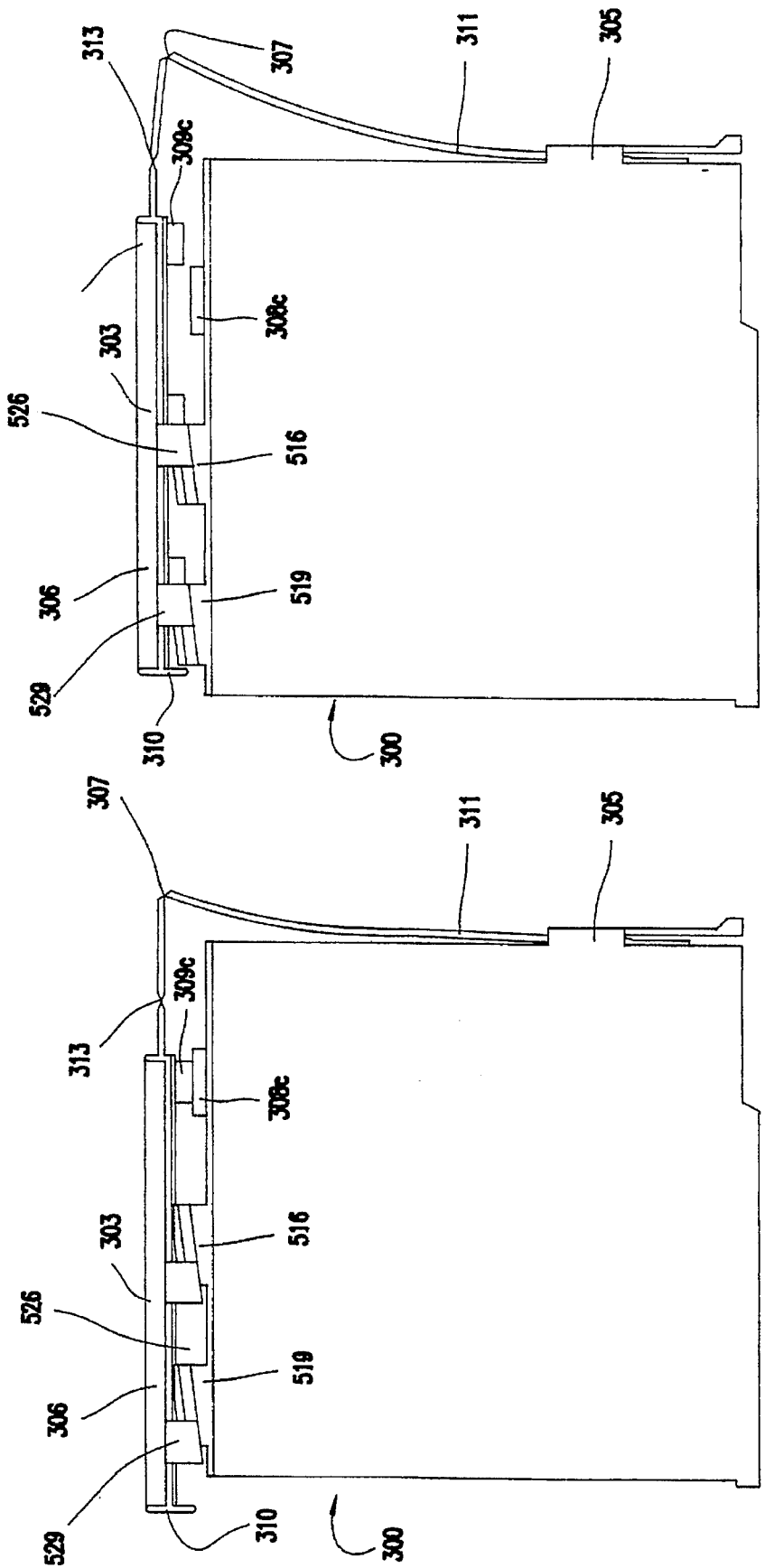

SELF-SEALING REAGENT CONTAINER AND REAGENT CONTAINER SYSTEM

BACKGROUND OF THE INVENTION

1. Field of the Invention

The invention generally relates to a self-sealing reagent container, and a reagent container system particularly well-suited for dispensing and preserving chemical or biochemical reagents for use in an automated analyzer.

2. Description of the Prior Art

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentrations of drugs, hormones, polypeptides, or other analyte compounds found in a test sample. For many years, immunoassays were performed by hand by trained laboratory technicians.

Recently, many companies have begun producing automated immunoassay analyzers. Automating the immunoassay procedures can be onerous because of the large number of steps needed to be executed. For example, in a conventional scheme, a sample is mixed with a reagent and a solid support having a bound antigen or antibody, the sample is incubated such that the corresponding antigen or antibody in the sample and a labeled antigen or antibody provided in the reagent can be bound to the antigen or antibody on the solid support, then the solid support is thoroughly washed and the label (fluorescent, radioactive, chemiluminescent, or the like) is detected by an appropriate mechanism, and finally the analyte of interest (antigen or antibody) is quantified from the detected label.

Most of today's automated immunoassay analyzers are designed for "walk away" operation, where the technician loads sample containing tubes onto a carousel and presses a start button. Thereafter, the automated immunoassay analyzer mixes appropriate reagents (often stored aboard the analyzer) with the sample, performs incubating and washing operations, detects the label, and computes the quantity of analyte in the sample from the detected label and stored calibration curves. The entire operation is typically done under computer control, and in some automated immunoassay analyzers, bar coding is used to identify the sample under test. The results of the immunoassays are typically output onto computer paper for inspection by the technician, or monitored and displayed in real time as described in U.S. Pat. No. 5,316,726(Babson et al).

One conventional technique and system for automated immunoassay, described in commonly assigned U.S. Pat. No. 5,316,726(Babson et al.), includes means for selecting a reagent involving a reagent carousel with an associated bar code reader, where the selecting means can include means for periodically determining a position for each reagent on the reagent carousel. The reagent carousel described in U.S. Pat. No. 5,316,726 has slots each of which holds a reagent bottle, and each reagent bottle has bar coded identifying means to allow identification of the bottle's contents.

A known reagent vessel and sealing mechanism sold by Organon Teknika involves side-by-side reagent compartments in wedge shapes that are fitted with a common reagent vessel cover including an access hole to each compartment. Track means are integrally formed on the cover to hold and guide a slidable lid back and forth across the access holes to cover the access holes, or expose same through alignment with via holes in the lid. The lid loosely sits flat on the cover surface in this device. The lid is attached loosely to the cover surface to reduce friction during movement of the lid back-and-forth over the cover surface. This loose attachment of the lid precludes tight sealing of the contents of the reagent vessel. External force must be provided to push the lid to an open position by sliding it along the cover track until holes in the lid align with access holes in the reagent vessel cover. After completing withdrawal of reagent, the return force after opening the lid is supplied by a metal coil spring which moves the lid back into the closed position (i.e., misaligning the cover and lid holes).

Another known reagent vessel and sealing mechanism sold by Abott Laboratories involves providing an individual flip-up hinged cover for each compartment opening of the reagent vessel. The flip up lids are living hinges that each involve a cap that pivots about a hinge adjacent the reagent compartment access opening such that the cap can be translated through an arc extending from a horizontal position directly over the reagent compartment opening to an upright position, and back. These lids require an external force to be pushed upward to the upright position and thus exposing the reagent compartment opening. A reagent withdrawing device can be inserted through the opening to extract reagent, and once the reagent withdrawing device clears the access opening of the reagent compartment, the lid partly descend backs over the opening on its own accord by virtue of the living hinge. However, an external force is needed to tightly reseal the lid on the mouth of the opening. The provision of such individual living hinges for each reagent compartment opening is relatively complicated and expensive.

SUMMARY OF THE INVENTION

It is an object of this invention to provide a reagent container with a self-sealing lid mechanism to allow storage and preservation of different reagents while enabling intermittent ready access to the various reagent contents held therein and self-sealing action by the lid mechanism after completing the reagent extraction.

It is another object of the invention to provide a system comprising a plurality of reagent containers as supported on a common carousel such that a large number and wide diversity of reagents are made available in a spatially efficient manner.

It is a further object of the invention to use the aforesaid reagent container system on board an automated immunoassay analyzer to provide a readily accessible supply of many different types of reagents, thereby enhancing the versatility of the analyzer as it is capable of handling a wider range of different tests.

According to the invention, a unique reagent container device is utilized being a multi-compartmented vessel having reagent contents thereof accessible via a self-sealing lid means that functions according to a "living hinge" principle. That is, the lid means generally is a hinged appendage having a substantially vertical arm attached at its lower end to the wall of the reagent vessel and a substantially horizontal arm located above the upper surface of the reagent vessel. The horizontal arm has alternating caps and openings along its length to permit sealing and unsealing of underlying vessel compartment openings, depending on the location of the horizontal arm over the upper surface of vessel. The horizontal and vertical arms of the lid means are connected by the hinge which is the point of flexure.

The lid is subject to a normal bias force generated by a bend formed in vertical arm located below the hinge which causes the horizontal arm to move into a normal position where its sealing caps normally align with underlying reagent compartment openings to seal same. However, by application of an external force from a direction opposite to the normal bias acting on the horizontal arm and adequate to exceed the normal bias force acting on the horizontal arm, the lid can be displaced by an operator or by electromechanical actuator means to uncover the caps from the compartment opening to align the access openings provided in the horizontal arm with openings in the compartments vessels to permit reagent extraction therefrom. Once the extraction means is removed from the compartment opening the normal bias on the horizontal arm acts to move the horizontal arm back to its normal position so as to reseal the vessel compartment openings with the caps.

Therefore, the lid means is biased to provide automatic self-sealing action such that the lid reseals access holes of the multi-compartmented vessel once a reagent extraction device clears the access holes of the vessel compartment openings and openings provided in the lid.

Another aspect of the reagent sealing device of this invention is that the alternating caps and openings in the horizontal arm of the lid means are maintained in translational alignment over the openings of the reagent vessel compartments by use of guide means to restrict sideways movement of the horizontal arm. In one preferred embodiment, a pair of hooks is provided on the opposing sides of the bottom of the horizontal arm which mechanically interlock with and are capable of intersliding movement with an opposing hooked ramp guide means provided on the upper surface of the vessel compartments. The ramp guide means preferably are inclined at a small angle such that when external force is applied to push the horizontal arm backward to align the horizontal arm holes with vessel holes for reagent extraction procedures, the horizontal arm travels slightly upward such that the caps do not frictionally engage or contact the upper surface of the vessel compartments during this displacement. The guide means thus serves two functions of guiding the direction of horizontal motion of the horizontal arm and also to restrain and delimit vertical movement of the horizontal arm as it translates up and down the ramp guide means.

The lid means can be pre-installed, or attached to the reagent storage vessel by the operator on site, to become an integral member thereof. Moreover, a plurality of the reaction containers can be arrayed together on a common carousel to allow for selective picking and accessing of a desired type of reagent from the collection of reagents.

Therefore, since discrete, individual bottles of reagents need not be used in this invention, a spatially efficient arrangement of the reagents on a carousel can be utilized and reagent container identification requirements are mitigated while still enabling the immunoassay analyzer to accommodate a large number of tests encompassing many diverse analytes, each requiring their own appropriate reagents. Also, since the cover is self-sealing, the need to apply external forces from varying directions need not be provided to move the cover to allow both opening and resealing of reagent vessels.

BRIEF DESCRIPTION OF THE DRAWINGS

The foregoing and other objects, aspects and advantages will be better understood from the following detailed description of the preferred embodiments of the invention with reference to the drawings, in which:

FIG. 7 is a side exterior view of a reagent container with a re-sealable lid of the invention in a closed position; and FIG. 8 is a side exterior view of a reagent container with a re-sealable lid of the invention in an open position.

DETAILED DESCRIPTION OF THE PREFERRED EMBODIMENTS OF THE INVENTION

The reagent container device and reagent container device system of the present invention are a subsystem of an analytical instrument intended to produce reportable assay results through the processing of specimens and various other components of the chemistry system. This processing involves the control and timing of various internal operations as well as the acquisition and processing of data generated internally or through interaction with an external computer system such as LIS. The analytic instrument is an integrated electromechanical apparatus which processes specimens in order to generate test results. It is comprised of all the mechanical hardware, electronic hardware and software required to perform either the chemical or the immunoassays desired.

Figure 2:
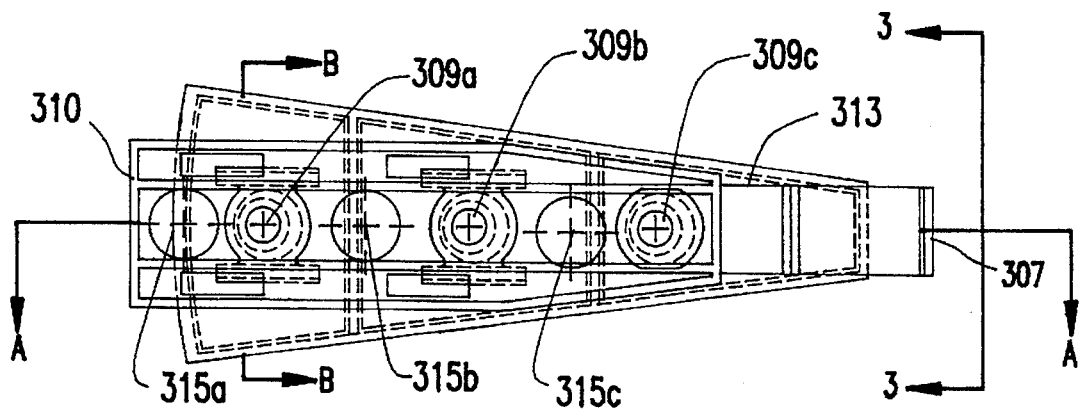
FIG. 2 is a top view of the reagent container with re-sealable lid of FIG. 1.
Figure 1:
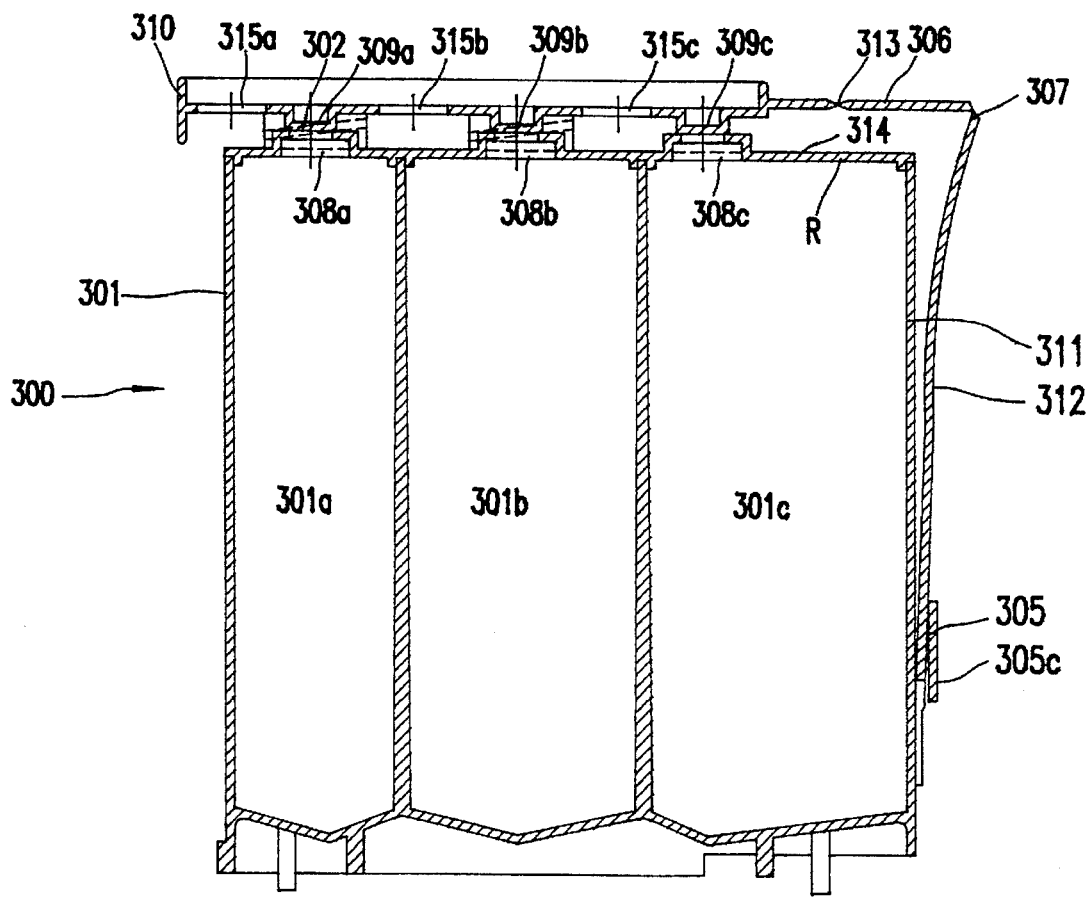
FIG. 1 is a fragmentary cross-sectional side view of a reagent container with re-sealable lid of the invention.

Referring now to the drawings, and more particularly to FIG. 1, there is shown a reagent container 300 of the invention with its self-sealing lid mechanism 303 attached thereto. The container 300 itself has a reagent vessel 301 comprised of a plurality of separate reagent storing compartments or wells, indicated as three compartments in this example of 301a, 301b, and 301c. These compartments share a common cover 314, which provides compartment openings 308a, 308b, and 308c, respectively. The openings 308a–c have a size adequate to permit a reagent extracting pipette (not shown) to be introduced into and retracted from the compartment in an unencumbered manner. The reagent container can have any convenient geometric shape. The reagent container 300 preferably is provided in an overall wedge-like shape, as indicated in the top view of FIG. 2, which allows a plurality of such reagent "wedges" to be situated side-by-side in a pie-like configuration on a carousel, thereby permitting a wide variety of reagents types to be accessible for immunoassay operations. Alternatively, the reagent compartments can be positioned in a linear array to provide an overall rectangular shaped reagent container.

The reagent vessel 301 can be prepackaged with its compartments pre-filled with selected reagents deposited in the various compartments. The openings can be optionally pre-sealed with a detachable adhesive-coated metallic foil. The reagent container can be loaded on a reagent carousel; sealing foil removed (if any); and then lid means 303 attached to the exterior of vessel 301, in a manner described in greater detail below.

An important aspect of the invention resides in the self-sealing lid means 303 which automatically reseals the reagent container 300 between any intermittent reagent extractions from the container without the need for external force to be applied to effect re-closure. The lid means 303 is a molded plastic member with spring-like biasing force generated by a bend 316 located below the hinge 307 that compels the lid means to release any bias force by movement of the horizontal arm 306 along the x-direction towards projection 310 until caps 309a–c cover openings 308a–c to return lid means 303 to a "closed" position (see FIG. 7).

Figure 4:
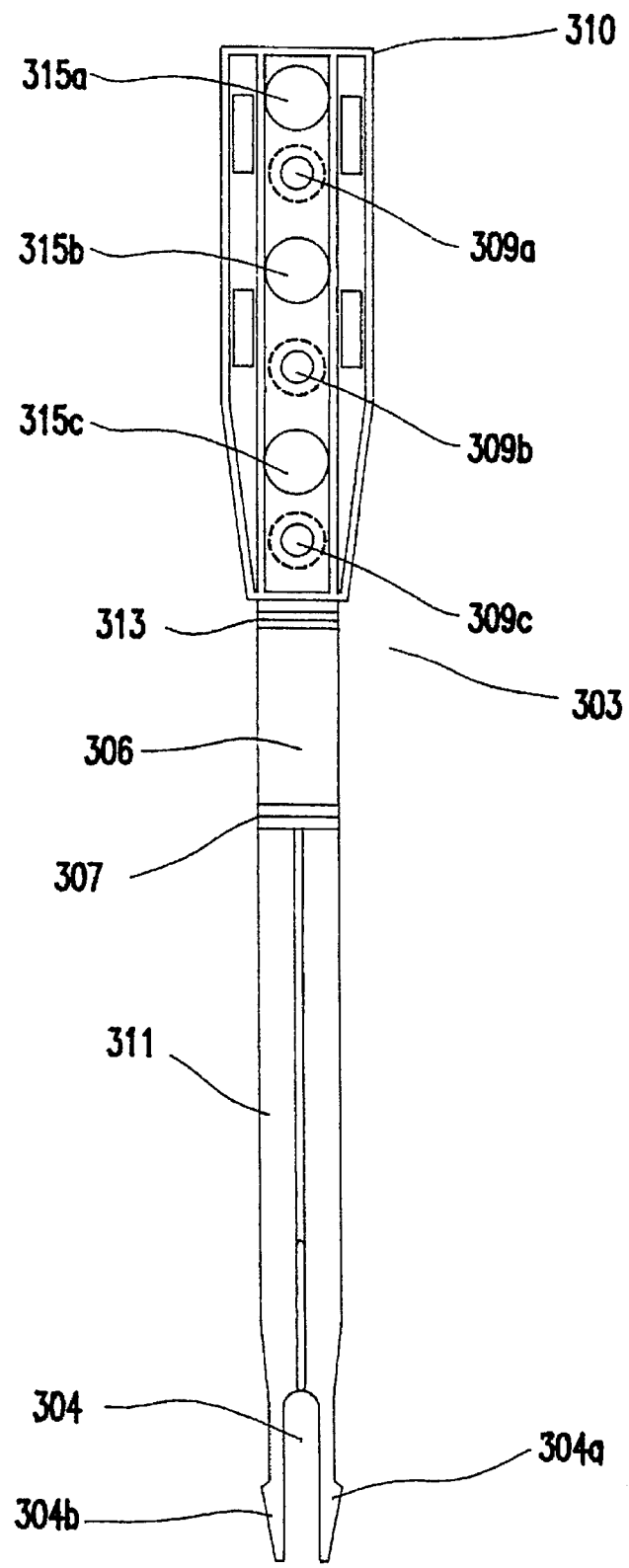
FIG. 4 is a fragmentary top view of the lid means of the invention.

When external force is supplied to projection 310 in the x-direction adequate to overcome the normal bias force acting in the opposite direction, the arm 306 displaces rearward in the direction of hinge 307 until caps 309a–c are pushed far enough to horizontally clear the underlying compartment openings 308a–c. As can be more easily seen in FIG. 4, the lid caps 309a–c alternate with openings 315a–c. Depending on the location of arm 306, either the caps 309a–c or openings 315a–c can be aligned with the underlying openings 308a–c in the cover 314 of the reagent vessels. The caps 309a–c are sized slightly larger in diameter than openings 308a–c, respectively, such that the caps cover the openings when the lid means is in its normal position, versus its active position (described in greater detail below). As best seen in FIG. 4, a second hinge 313 is provided at a location approximately midway between opening 315a and hinge 307. Hinges 307 and 313 can be formed as thinned portions in the lid means 303 during its molding. The first hinge 307 allows the arm 306 to generally slide forwards and backwards. The second hinge 313 relieves stress created in the arm 306 when it is pushed backwards while traversing and restrained by the ramp guide means 51a, 51b (FIG. 5) such that the arm 306 can retract along a horizontal line without tending to significantly arc (see FIG. 8). Both hinges 307 and 313 are formed as thinned plastic regions in the arm molding which form flexure points along the arm 311 and arm 306, respectively. The thickness of the hinge must left sufficiently thick to prevent failure of the crimped or thinned hinge-like portion after only limited numbers of flexures.

The lid means 303 also is attached to the side wall 312 of reagent vessel 301 at its lower end. The lid means 303 can be preassembled with the reagent vessel or attached on site when used. For example, when a fresh reagent wedge 300 is provided to a carousel of an immunoassay analyzer, the protective foil can be stripped from the upper surfaces of openings 308a–c to expose openings 308a–c, and the lid means 303 can be attached to the container before or after these steps.

Another aspect of the reagent container sealing system 303 of this invention is that the alternating caps 309a–c and openings 315a–c in the horizontal arm 306 of the lid means 303 are maintained in translational alignment over the underlying openings 308a–c of the reagent vessel compartments by use of guide means (not shown in FIG. 1 for sake of clarity as to other above-discussed features) to restrict sideways movement of the horizontal arm 306 during its movement over the upper surface of cover 314.

Figure 5:
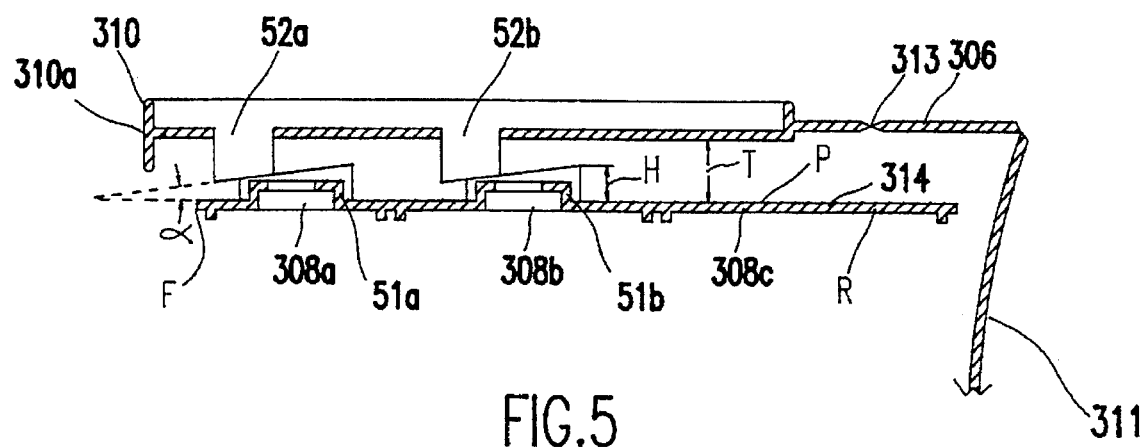
FIG. 5 is a fragmentary side view along direction A—A of FIG. 2 of the of the self-sealing horizontal arm of the lid means and ramp guide means system of the present invention.

As seen in FIG. 5, ramp guide means 51a and 51b are provided on the upper surface of cover 314. Some features of the lid means and reagent vessel, not essential to understanding this aspect of the invention, have been omitted from FIG. 5 to clarify the illustration. The ramps 51a and 51b, and corresponding lid projections 52a and 52b, are inclined at the same relatively small acute angle α relative to the horizontal plane P extending coplanar with the upper flat surface portion of cover 314, such as inclined from the horizontal direction (i.e., the x-direction) at angle ranging from about 5° to 15°, preferably about 10°. The direction of inclination of the ramp guide means 51a, 51b steeps up from the front F of cover 314 towards the rear R of cover 314.

The acute angle α established for ramps 51a and 51b (and projections 52a and 52b) must be large enough such that as soon as lid means 303 is pushed rightward along the x-direction via force applied at projection 310 (in the perspective of FIG. 5), that the caps 309a–c of lid means 303 are contemporaneously translated upward up the ramps 51a and 51b and out of contact with the surfaces of the cap openings 308a–c of the cover 314. Thus, sliding friction between the cover 314 and lid means 303 is avoided without resorting to a loose interfit of lid 303 and cover 314. On the other hand, the acute angle α of the ramps 51a and 51b must be not be set too large so as to make access difficult to openings 309a–c of cover 314 when lid means 303 is pushed rightward along the x-direction via force applied at projection 310. That is, with an ever steeper angle for ramps 51a and 51b, the horizontal profile of openings 315a–c in the lid 303 is diminished.

Figure 6:
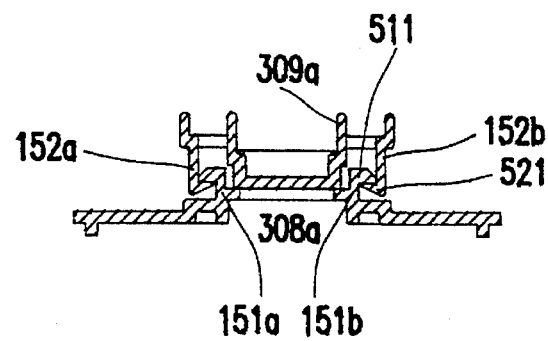
FIG. 6 is a fragmentary end view along direction B—B Of FIG. 2 showing an interlocking ramp guide means and horizontal arm system for the lid means.

The ratio of the vertical height H of the ramps 51a, 51b, relative to overall gap T between arm 306 and cover 314, that is, the ratio H/T, is about 40–50% for the highest point of each ramp and about 5–15% at the lowest end of each ramp. The arm 306, when horizontally displaced over the upper surface of cover 314, is mechanically guided by ramp means 51a, 51b via downward projections 52a, 52b on arm 305 having means to interconnect with the ramp means 51a, 51b while permitting intersliding movement along a single line of direction. For example, as shown in FIG. 6, interlockable hooks can be integrally formed on the ends of projections 52a, 52b and ramps 51a and 51b to allow slidable interfitting of these components. In more detail, projection 52a actually is comprised of a pair of projections 152a and 152b located on opposite sides of the related cap 309a on arm 306. Similarly, ramp guide means 51a, is actually comprised of a pair of upstanding members 151a and 151b extending from cover 314 on either side of cover opening 308a. Projection 152b, like its companion projection 152a, terminates in a downward projecting hook 521 which mechanically interfits with an upstanding hook or rail 511 formed in ramp guide portion 151b.

Therefore, an important aspect of the invention is that when force is applied to projection 310 in the x-direction by an operator or electromechanical actuator, the projections 52a and 52b will slide up ramp guide means 51a and 51b, respectively, avoiding sliding friction without resorting to loose interfit between the lid 303 and cover 314. Preferably, when access to the reagent compartments is desired, projection 310 is horizontally pushed with adequate force to overcome the normal opposing bias force in the lid means 303 caused by spring-arm 311 until caps 309a–c in the arm 306 clear compartment openings 308a–c and openings 315a–c instead align over the compartment openings 308a–c.

Figure 3:
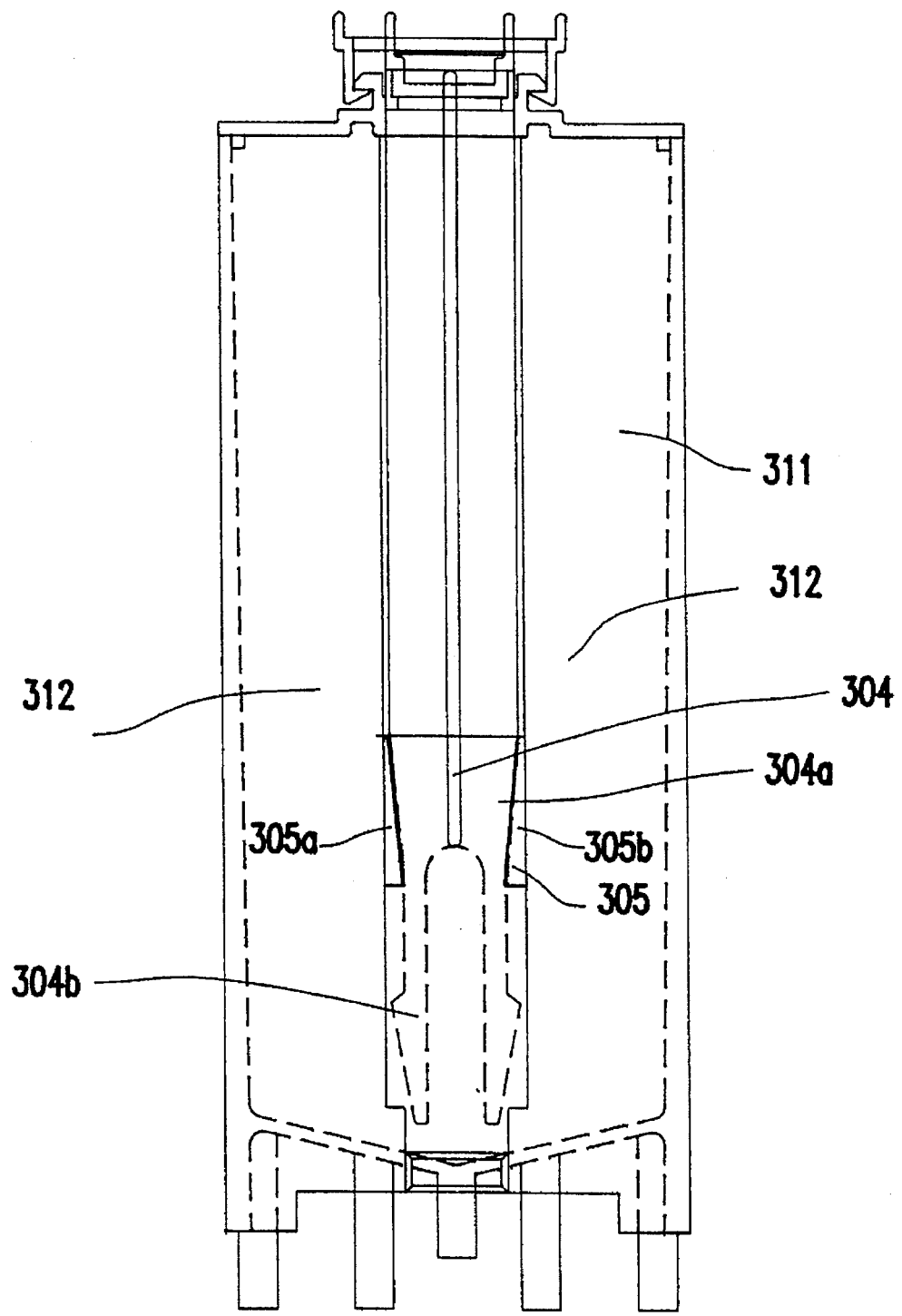
FIG. 3 is a rear view of the reagent container and re-sealable lid along the direction 3—3 indicated in FIG. 2.

The lower end of arm 311 of lid means 303 can be attached to the sidewall 312 of the reagent vessel by any convenient means. As one technique to attach the arm 311 of lid means 303 to the inner vertical sidewall 312 of the reagent container 300, as shown in FIG. 3, the inner vertical wall 312 of the reagent vessel 301 can have a sleeve 305 comprised of two upstanding walls 305a and 305b, which define an opening sized to receive tongue member 304 of arm 311 of lid 303, and a cover side 305c (see FIG. 1) integral with side walls 305a, 305b which prevents prevents movement of the arm off the sidewall 312. The tongue member 304 has a pair of prongs 304a and 304b that are normally biased outward in the y-direction, but which can be displaced inward in the y-direction by operator handling.

FIG. 4 is a fragmentary view of the lid means 303 alone, where the labeled elements have the descriptions set forth herein. The prongs 304a and 304b of tongue 304 of the lid means, are inserted into the sleeve 305 through opening 313 to grip the respective walls 305a and 305b due to the outward spring-like bias of the prongs 304a and 304b, to attach the lid means 303 to the reagent vessel 301. Ribs or flanges (not shown) also can be formed on the inner sides of walls 305a and 305b of sleeve 305 to mechanically enhance the interlock between the tongue 304 and sleeve 305. The reagent wedges, i.e., "reagent packs", of the invention will simultaneously support a relatively large number of assay types, e.g., up to 24 or more, each requiring up to 3 or even more liquid reagents, without reduction of the on-board assay capacity of an automated chemical/biochemical analyzer. The reagent packs of the invention also provide the ability to store and preserve reagents on-board an immunoanalyzer, for example, for relatively extended periods of time, e.g. one month, without detectable degradation. The reagent packs of the invention also permit reagents to be positively identified via an attached bar code.

A rotating carousel accommodates a plurality of wedge-shaped reagent packs, each reagent pack capable of holding a plurality of different reagents in different compartments thereof. These packs include instrument actuated covers as well as vertical bar codes which are accessible to the specimen and diluent bar code reader. The entire carousel is housed within a refrigerator chamber maintained at about 4° C.

By way of illustration, in immunoassay analysis, the reagents are supplied in liquid form, and are used to generate a detectable signal proportional or inversely proportional to the concentration of analyte in a specimen. During processing, they are deposited into individual reaction tubes associated with a bead having an appropriate biomaterial coated on its surface for the test needed on the sample. Reagents are contained within disposable packs, each bearing a plurality, e.g., up to three or more, different reagents in separate respective compartments. These packs protect their contents from the environment by virtue of their instrument actuated lids and their construction from colored transparent materials. The packs are also constructed of a material, such as plastic, that is sufficiently translucent to permit operators to visually observe from the outside the fluid levels within.

A plurality, e.g., up to 24 or more, of different reagent packs can be simultaneously resident on the analyzer instrument, and the operator may replace or supplement the supply of packs at any time. A quantity of reagent may be consumed from one or more of the chambers of a reagent pack for each test conducted. A particular reagent pack may be used for several different test types, but reagent/bead lot matching is required for each test type the reagent pack supports. A given test must use reagents from one and only one type of reagent pack. More than one pack of a given type may be resident on the analyzer instrument simultaneously. Reagent packs serve the following functions:

a) to protect the reagents they contain from evaporation;
b) to protect the reagents they contain from contamination;
c) to package the reagents in a manner convenient for operator access and handling;
d) to facilitate the dispensing of reagents into each reaction tube as needed;
e) to provide the necessary space for attachment of labeling; and
f) to enable visual estimation of reagent inventory by the operator.

Reagent packs can be bar code labeled with all the information needed to identify them to both an analyzer instrument and the operator.

By way of example, the basic overall series of steps use to perform a immunoanalysis test on a sample of interest with use of the reagent container system of this invention, can be typified as follows:

a) deposition of reaction tubes onto a reaction tube load chain;
b) deposition of beads into reaction tubes using the inventive bead container system;
c) transfer reaction tubes from reaction tube load chain to a pipetting station for depositing the specimen (analyte of interest) and liquid reagent from a reagent container into the reaction tube (already containing the bead);
d) incubation and agitation of reaction tubes;
e) optional washing;
f) optional (e.g., chemiluminescent) susbtrate addition, incubation, addition of trigger compounds;
g) quantitation of analyte (e.g., by reaction tube light output measurement); and
h) discharge of spent tubes.

An analyzer using the reagent container system and scheme of the present invention represents a high throughput automated analyzer system capable of assaying a broad range of chemicals, or analytes in serum, plasma, and urine. It is also contemplated within the scope of the invention that specific chemistry kits might also handle clarified cerebrospinal fluid or saliva. Also, the system can impart a high degree of automation to a diverse set of immunoassays, such as encountered in hospital and commercial laboratory settings. As such, high volume testing (up to even 200 tests results per hour) is expected and must be accommodated. In addition, the urgency of medical decisions that will depend on the results of these assays dictates a rapid analytical response time.

Although the reagent container system has been exemplified in terms of an immunoanalysis environment, it will be understood that the reagent container system of this invention has general applicability encompassing chemical reagent storage in general, as an individual device, or as used on board an automated chemical or biochemical analyzer.

While the invention has been described in terms of its preferred embodiments, those skilled in the art will recognize that the invention can be practiced with modification within the spirit and scope of the appended claims.

We claim:

1. Self-sealing reagent container, comprising:

a vessel having a plurality of separate compartments defined by sidewalls and a cover as an upper surface, each compartment having an opening in said upper surface;

a self-sealing lid attached to the exterior of a sidewall of said vessel, comprising:

a first arm confronting said upper surface of said vessel, said first arm supporting a plurality of caps interspaced by openings extending through said arm, said first arm capable of reciprocal movement over said upper surface of said vessel to permit covering and uncovering of said compartment openings by said caps, a second arm confronting said exterior sidewall of said vessel, said second arm having a lower end attached to said sidewall of said vessel and an upper end connected to said first arm via a first hinge, guide means maintaining reciprocal displacement of said first arm along a single horizontal line of movement, and whereby said first arm of said lid is subject to a normal bias force created by said second arm whereby said plurality of caps normally covers said compartment openings, wherein when a horizontal external force is exerted in opposition to and adequate to exceed said normal bias force said first arm being capable of horizontal displacement adequate to uncover said caps from said compartment openings, and upon removal of said horizontal external force said normal bias force acting on said first arm of said lid to re-cover said compartment openings with said caps.

2. The self-sealing reagent container of claim 1, further comprising a projection extending from a rear said cover so as to deflect said second arm rearward sufficient to create a spring force in said lid.

3. The self-sealing reagent container of claim 1, wherein said guide means comprises ramp guides on said cover and projections from said first arm that mechanically, slidably interfit.

4. The self-sealing reagent container of claim 3, wherein said ramp guides are inclined at a nonzero angle relative to said cover.

5. The self-sealing reagent container of claim 4, wherein said nonzero angle ranging from about 5° to about 15°.

6. The self-sealing reagent container of claim 4, wherein said projections are capable of sliding up and down said ramp guide.

7. The self-sealing reagent container of claim 1, wherein said vessel has at least three compartments.

8. The self-sealing reagent container of claim 1, further comprising liquid reagents present in said compartments.

9. The self-sealing reagent container of claim 1, wherein said first hinge comprises a flexure point at a juncture between said first arm and said second arm.

10. The self-sealing reagent container of claim 1, wherein said lid is comprised of plastic.

11. The self-sealing reagent container of claim 1, further comprising a sleeve on said exterior sidewall of said vessel to mechanically engage prongs provided at a lower end of said second arm of said lid.

12. The self-sealing reagent container of claim 1, wherein said sleeve on said exterior sidewall of said vessel comprises flanges to mechanically engage said prongs of said tongue.

13. The self-sealing reagent container of claim 1, wherein said first arm further comprises a second hinge located intermediate said openings and said first hinge.

14. The self-sealing reagent container of claim 13, wherein said second hinge comprises a flexure point along said first arm.

15. A reagent container system, comprising:

a plurality of reagent containers removably fitted onto a common carousel, each said reagent container comprising:

a vessel having a plurality of separate compartments, each compartment having an opening in an upper surface of said vessel, and a sleeve on an exterior sidewall of said vessel;

a self-sealing lid attached to said vessel, comprising:

a first arm confronting said upper surface of said vessel, said first arm supporting a plurality of caps interspaced by openings extending through said arm, said first arm capable of reciprocal movement over said upper surface of said vessel to permit covering and uncovering of said compartment openings by said caps, and a second arm confronting said exterior sidewall of said vessel, said second arm having a lower end attached to said sidewall of said vessel and an upper end connected to said first arm via a hinge, guide means maintaining reciprocal displacement of said first arm along a single horizontal line of movement; and whereby said first arm of said lid is subject to a normal bias force created by said second arm whereby said plurality of caps normally covers said compartment openings, wherein when a horizontal external force is exerted in opposition to and adequate to exceed said normal bias force said first arm being capable of horizontal displacement adequate to uncover said caps from said compartment openings, and upon removal of said horizontal external force said normal bias force acting on said first arm of said lid to re-cover said compartment openings with said caps.

16. The reagent system of claim 14, wherein said carousel is rotatable.

17. The reagent system of claim 14, wherein said reagent containers each include an identifying means.

18. The reagent system of claim 16, wherein said identifying means comprises a readable bar code.

* * * * *